(12) United States Patent
Qian et al.

(10) Patent No.: US 10,627,985 B2
(45) Date of Patent: Apr. 21, 2020

(54) MANIPULATION OF A VIRTUAL OBJECT DURING A CONVERSATIONAL SESSION

(71) Applicant: Lenovo (Singapore) Pte. Ltd., Singapore (SG)

(72) Inventors: Ming Qian, Cary, NC (US); John Weldon Nicholson, Cary, NC (US); Song Wang, Cary, NC (US); David Alexander Schwarz, Morrsville, NC (US)

(73) Assignee: Lenovo (Singapore) Pte. Ltd., Singapore (SG)

( * ) Notice: Subject to any disclaimer, the term of this patent is extended or adjusted under 35 U.S.C. 154(b) by 9 days.

(21) Appl. No.: 15/625,618

(22) Filed: Jun. 16, 2017

(65) Prior Publication Data

US 2018/0364884 A1 Dec. 20, 2018

(51) Int. Cl.
| | |
|---|---|
| *G06F 3/00* | (2006.01) |
| *G06F 3/0481* | (2013.01) |
| *G06F 3/0484* | (2013.01) |
| *G06F 3/16* | (2006.01) |
| *G06F 3/01* | (2006.01) |
| *G06T 19/00* | (2011.01) |
| *G16H 40/63* | (2018.01) |
| *G16H 50/50* | (2018.01) |

(52) U.S. Cl.
CPC .......... *G06F 3/04815* (2013.01); *G06F 3/011* (2013.01); *G06F 3/016* (2013.01); *G06F 3/04845* (2013.01); *G06F 3/167* (2013.01); *G06F 3/04842* (2013.01); *G06T 19/006* (2013.01); *G16H 40/63* (2018.01); *G16H 50/50* (2018.01)

(58) Field of Classification Search
CPC ...... G06F 17/50; G06F 3/04815; G06F 3/011; G06F 17/5004; G06F 3/012; G06F 3/013; G06F 2217/04; G06F 3/017; G06F 3/0484; G06F 19/00; G06F 3/0304; G06F 3/0481; G06F 3/04817; G06F 3/0482; G06F 17/212; G06F 17/30864; G06F 17/30905; G06F 3/005; G06F 3/0346; G06F 3/04812; G06F 3/04842; G06F 3/04847; G06F 3/0486; G06F 8/61; G06F 11/1612; G06F 11/1666; G06F 11/302; G06F 11/321

See application file for complete search history.

(56) References Cited

U.S. PATENT DOCUMENTS

| | | | | |
|---|---|---|---|---|
| 2010/0299616 | A1* | 11/2010 | Chen | G06Q 10/10 715/753 |
| 2011/0087463 | A1* | 4/2011 | Nakhle | G06F 17/5095 703/1 |
| 2011/0245708 | A1* | 10/2011 | Finkel | A61B 5/0484 600/544 |

(Continued)

*Primary Examiner* — Di Xiao
(74) *Attorney, Agent, or Firm* — Ference & Associates LLC (57) ABSTRACT

One embodiment provides a method, including: receiving, at an information handling device, an indication to display a virtual object in association with a conversational session; receiving, during the conversational session, user manipulation input associated with the displayed virtual object; and performing, based upon the received user manipulation input, at least one function associated with the virtual object. Other aspects are described and claimed.

17 Claims, 3 Drawing Sheets

(56) References Cited

U.S. PATENT DOCUMENTS

| | | | |
|---|---|---|---|
| 2016/0179336 A1* | 6/2016 | Ambrus | G02B 27/017 |
| | | | 715/768 |
| 2016/0357258 A1* | 12/2016 | Yeom | G06F 3/016 |
| 2017/0068774 A1* | 3/2017 | Cluckers | A61B 5/743 |
| 2018/0025724 A1* | 1/2018 | Hunt | G06F 17/30867 |

* cited by examiner

MANIPULATION OF A VIRTUAL OBJECT DURING A CONVERSATIONAL SESSION

BACKGROUND

Information handling devices ("devices"), for example smart phones, tablet devices, smart speakers, laptop and personal computers, and the like, may be capable of receiving user command inputs and providing outputs responsive to the input. Generally, a user interacts with a voice input module, for example embodied in a digital assistant through use of natural language. This style of interface allows a device to receive voice inputs from a user, process those inputs, and provide audible outputs according to preconfigured output settings. Advances in technology have enhanced user's ability to visualize and/or interact with virtual objects using augmented reality ("AR") or virtual reality ("VR") techniques. It would be desirable to incorporate these AR/VR techniques into interactions with a digital assistant.

BRIEF SUMMARY

In summary, one aspect provides a method, comprising: receiving, at an information handling device, an indication to display a virtual object in association with a conversational session; receiving, during the conversational session, user manipulation input associated with the displayed virtual object; and performing, based upon the received user manipulation input, at least one function associated with the virtual object.

Another aspect provides an information handling device, comprising: a processor; a memory device that stores instructions executable by the processor to: receive an indication to display a virtual object in association with a conversational session; receive, during the conversational session, user manipulation input associated with the displayed virtual object; and perform, based upon the received user manipulation input, at least one function associated with the virtual object.

A further aspect provides a product, comprising: a storage device that stores code, the code being executable by a processor and comprising: code that receives an indication to display a virtual object in association with a conversational session; code that receives, during the conversational session, user manipulation input associated with the display virtual object; and code that performs, based upon the received user manipulation input, at least one function associated with the virtual object.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

The primary form of communication between people is audible natural language speech. Through speech people can engage in conversations, communicate ideas, describe feelings, describe visual perceptions (e.g., images, videos, etc.), and the like. Advances in technology have enabled users to use natural language speech ("voice input") to interact with their devices. One method of interacting with a device is to use digital assistant software employed on the device (e.g., Siri® for Apple®, Cortana® for Windows®, Alexa® for Amazon®, etc.). Digital assistants are able to provide outputs (e.g., audible outputs, visual outputs, etc.) that are responsive to a variety of different types of user inputs (e.g., voice inputs, etc.).

In various professional fields (e.g., medicine, law, information technology, customer service, etc.), a digital assistant may be used to perform general diagnostic functions associated with the field. For example, in the context of the medical field, a user may interact with a medically-tuned digital assistant (e.g., Digital Health Assistant® for WebMD®, etc.) to attain an electronic diagnosis based on patient input. The diagnosis may be attained, for example, through the audible communication of various symptoms in response to pointed questions from the medical digital assistant. As another example, in the context of the information technology field, a user may interact with a digital assistant in a chat window when providing a request for service or assistance.

Conventionally, existing implementations of digital assistants in professional fields are only able to utilize voice and/or text-based interaction. However, there are many instances when communication through audible speech or text alone may not be sufficient to adequately communicate an individual's point. For example, a patient may have a difficult time describing, in words, exactly where they feel the pain in their body, how intense the pain is, which internal organs the pain is proximate to, and the like. As another example, a person may find it difficult to communicate exactly what is wrong with a computer because the user is unsure of the proper terminology for different components.

Accordingly, an embodiment provides a method for communicating with an augmented virtual assistant that allows a user to communicate with the augmented virtual assistant in a variety of different ways. In an embodiment, an indication to display a virtual object may be received at a device. The virtual object may be, for example, a three-dimensional virtual representation of a part of the human body (e.g., a torso, etc.), a virtual representation of a device, or the like. The virtual object may be viewed on a device capable of displaying augmented reality data and/or virtual reality data. An embodiment may then receive manipulation input (e.g., selection input, rotation input, etc.) provided to the virtual object by a user and perform a corresponding function. For example, a user may rotate the virtual torso and select the portion of the virtual torso where they feel pain. Such a method may enhance interaction between a user and a digital assistant by providing the user with a greater capability to communicate their thoughts and feelings.

The illustrated example embodiments will be best understood by reference to the figures. The following description is intended only by way of example, and simply illustrates certain example embodiments.

Figure 1:
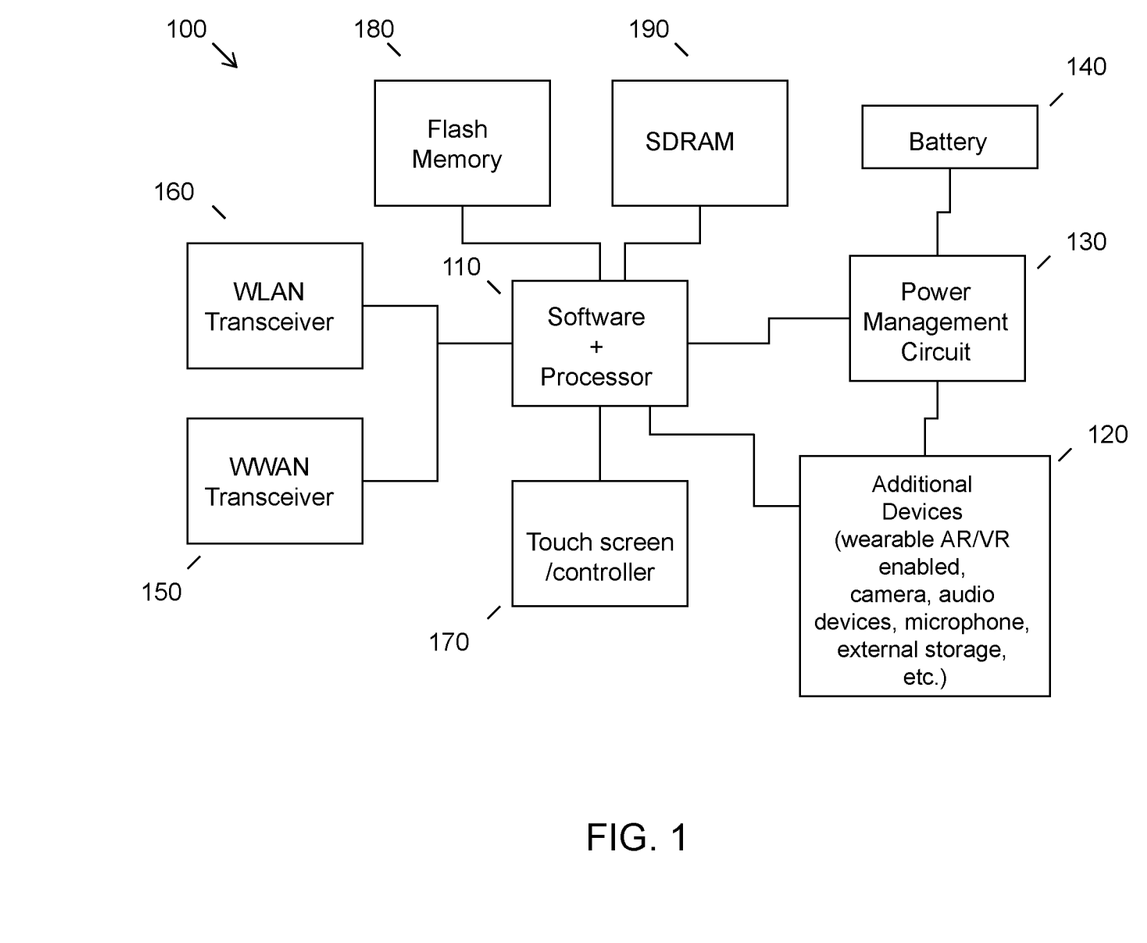
FIG. 1 illustrates an example of information handling device circuitry.

While various other circuits, circuitry or components may be utilized in information handling devices, with regard to smart phone and/or tablet circuitry 100, an example illustrated in FIG. 1 includes a system on a chip design found for example in tablet or other mobile computing platforms. Software and processor(s) are combined in a single chip 110. Processors comprise internal arithmetic units, registers, cache memory, busses, I/O ports, etc., as is well known in the art. Internal busses and the like depend on different vendors, but essentially all the peripheral devices (120) may attach to a single chip 110. The circuitry 100 combines the processor, memory control, and I/O controller hub all into a single chip 110. Also, systems 100 of this type do not typically use SATA or PCI or LPC. Common interfaces, for example, include SDIO and I2C.

There are power management chip(s) 130, e.g., a battery management unit, BMU, which manage power as supplied, for example, via a rechargeable battery 140, which may be recharged by a connection to a power source (not shown). In at least one design, a single chip, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additionally, devices 120 are commonly included, e.g., an image sensor such as a camera, audio capture device such as a microphone, a thermal sensor, etc. System 100 often includes a touch screen 170 for data input and display/rendering. System 100 also typically includes various memory devices, for example flash memory 180 and SDRAM 190.

Figure 2:
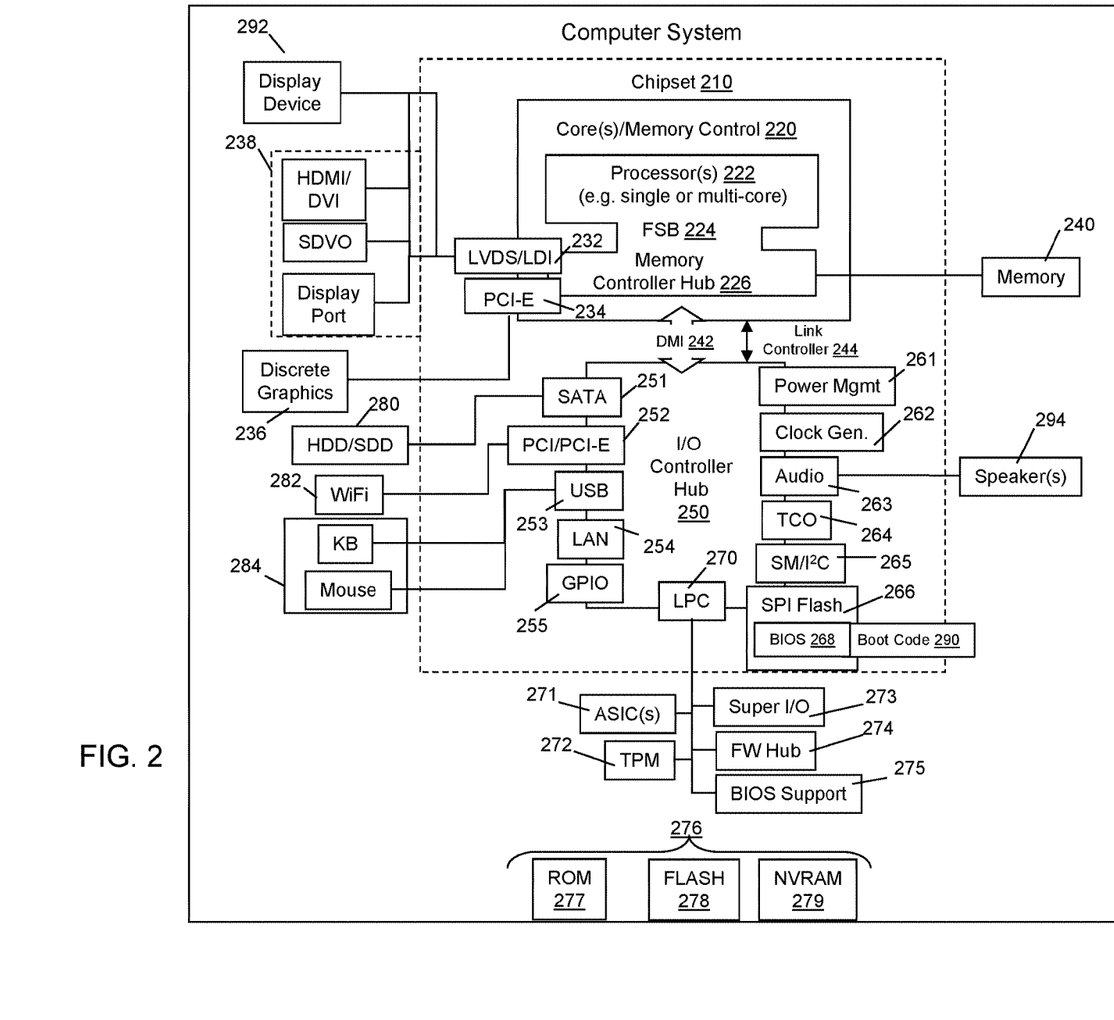
FIG. 2 illustrates another example of information handling device circuitry.

FIG. 2 depicts a block diagram of another example of information handling device circuits, circuitry or components. The example depicted in FIG. 2 may correspond to computing systems such as the THINKPAD series of personal computers sold by Lenovo (US) Inc. of Morrisville, N.C., or other devices. As is apparent from the description herein, embodiments may include other features or only some of the features of the example illustrated in FIG. 2.

The example of FIG. 2 includes a so-called chipset 210 (a group of integrated circuits, or chips, that work together, chipsets) with an architecture that may vary depending on manufacturer (for example, INTEL, AMD, ARM, etc.). INTEL is a registered trademark of Intel Corporation in the United States and other countries. AMD is a registered trademark of Advanced Micro Devices, Inc. in the United States and other countries. ARM is an unregistered trademark of ARM Holdings plc in the United States and other countries. The architecture of the chipset 210 includes a core and memory control group 220 and an I/O controller hub 250 that exchanges information (for example, data, signals, commands, etc.) via a direct management interface (DMI) 242 or a link controller 244. In FIG. 2, the DMI 242 is a chip-to-chip interface (sometimes referred to as being a link between a "northbridge" and a "southbridge"). The core and memory control group 220 include one or more processors 222 (for example, single or multi-core) and a memory controller hub 226 that exchange information via a front side bus (FSB) 224; noting that components of the group 220 may be integrated in a chip that supplants the conventional "northbridge" style architecture. One or more processors 222 comprise internal arithmetic units, registers, cache memory, busses, I/O ports, etc., as is well known in the art.

In FIG. 2, the memory controller hub 226 interfaces with memory 240 (for example, to provide support for a type of RAM that may be referred to as "system memory" or "memory"). The memory controller hub 226 further includes a low voltage differential signaling (LVDS) interface 232 for a display device 292 (for example, a CRT, a flat panel, touch screen, etc.). A block 238 includes some technologies that may be supported via the LVDS interface 232 (for example, serial digital video, HDMI/DVI, display port). The memory controller hub 226 also includes a PCI-express interface (PCI-E) 234 that may support discrete graphics 236.

In FIG. 2, the I/O hub controller 250 includes a SATA interface 251 (for example, for HDDs, SDDs, etc., 280), a PCI-E interface 252 (for example, for wireless connections 282), a USB interface 253 (for example, for devices 284 such as a digitizer, keyboard, mice, cameras, phones, microphones, storage, other connected devices, etc.), a network interface 254 (for example, LAN), a GPIO interface 255, a LPC interface 270 (for ASICs 271, a TPM 272, a super I/O 273, a firmware hub 274, BIOS support 275 as well as various types of memory 276 such as ROM 277, Flash 278, and NVRAM 279), a power management interface 261, a clock generator interface 262, an audio interface 263 (for example, for speakers 294), a TCO interface 264, a system management bus interface 265, and SPI Flash 266, which can include BIOS 268 and boot code 290. The I/O hub controller 250 may include gigabit Ethernet support.

The system, upon power on, may be configured to execute boot code 290 for the BIOS 268, as stored within the SPI Flash 266, and thereafter processes data under the control of one or more operating systems and application software (for example, stored in system memory 240). An operating system may be stored in any of a variety of locations and accessed, for example, according to instructions of the BIOS 268. As described herein, a device may include fewer or more features than shown in the system of FIG. 2.

Information handling device circuitry, as for example outlined in FIG. 1 or FIG. 2, may be used in devices such as AR/VR-enabled electronic devices, tablets, smart phones, personal computer devices generally, and/or electronic devices which may include digital assistants that a user may interact with and that may perform various functions responsive to receiving user input. For example, the circuitry outlined in FIG. 1 may be implemented in a tablet or smart phone embodiment, whereas the circuitry outlined in FIG. 2 may be implemented in a personal computer embodiment.

Figure 3:
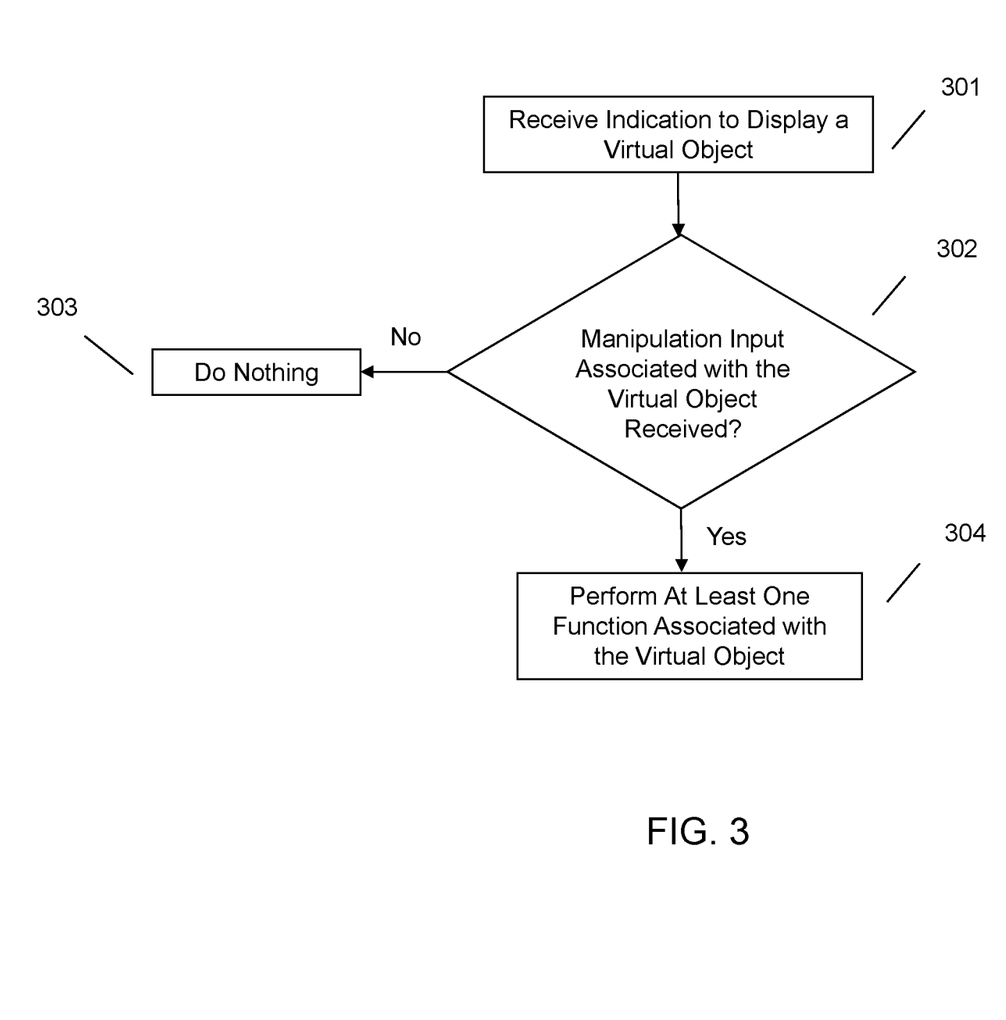
FIG. 3 illustrates an example method of providing manipulation input to a virtual object.

Referring now to FIG. 3, an embodiment may perform a function associated with a virtual object based upon received manipulation input. At 301, an embodiment may receive an indication to display a virtual object in association with a conversational session. The conversational session may include an interactive session with a digital assistant. For example, the user may access or request assistance from a digital assistant, which may trigger a virtual object to be displayed. As an example, a person may access a customer service site which may prompt presentation of a virtual object related to the request of the user. The conversational session may also include a session with another person. For example, a user may provide input to a device which may display a virtual object. The device may then transmit this information to another person. As an example, a user may access a medical assistance site and provide input regarding pain and symptoms, including input provided on a virtual object. This information, including a representation of the virtual object, may then be transmitted to a doctor on another device for the doctor to access and assess. For simplicity purposes, the subsequent discussion will be centered around a medically-based digital assistant (e.g., programmed and/or trained with medical terminology in order to perform symptom diagnostics, etc.). However, it should be understood that any type of digital assistant or conversational session agent may be used, for example, a customer service digital assistant, an information technology digital assistant, and the like.

In an embodiment, the indication may be received automatically without additional user input. For example, the indication may be received when an application, or a feature within an application, is launched or activated (e.g., when the digital assistant is activated). In an embodiment, the indication may be associated with a user command. The user command may be provided to a digital assistant disposed on an electronic device. For example, the command input may be received at an input device (e.g., physical keyboard, on-screen keyboard, audio capture device, image capture device, video capture device, etc.) and may be provided by any known method of providing input to an electronic device (e.g., touch input, text input, voice input, etc.). For simplicity purposes, the majority of the discussion herein will involve a voice input command that may be received at an input device (e.g., a microphone, a speech capture device, etc.) operatively coupled to a speech recognition device. However, it should be understood that generally any form of user input may be utilized. In an embodiment, the speech recognition device may or may not contain a display screen.

In an embodiment, the input device may be an input device integral to the speech recognition device. For example, a smart phone may be disposed with a microphone capable of receiving voice input data. Alternatively, the input device may be disposed on another device and may transmit received voice input data to the speech recognition device. For example, voice input may be received at a smart speaker that may subsequently transmit the voice data to another device (e.g., to a user's smartphone for processing, etc.). Voice input data may be communicated from other sources to the speech recognition device via a wireless connection (e.g., using a BLUETOOTH connection, near field communication (NFC), wireless connection techniques, etc.), a wired connection (e.g., the device is coupled to another device or source, etc.), through a connected data storage system (e.g., via cloud storage, remote storage, local storage, network storage, etc.), and the like.

In an embodiment, the virtual object may be a three-dimensional virtual object. The three-dimensional virtual object may be viewable on a device capable of displaying augmented reality data (e.g., Google Glass®, Microsoft HoloLens®, a smartphone, etc.), virtual reality data (e.g., Oculus Rift®, Samsung Gear VR®, etc.), and the like. In an embodiment, the virtual object may essentially be any object. For purposes of this disclosure, the virtual object described throughout the application will be a representation of a human body part (e.g., a human torso, etc.). The virtual body part may be a stock body part. For example, a digital assistant may access a database comprising pre-existing representations of different body parts (e.g., torsos, arms, legs, etc.). Alternatively, the virtual body part may be associated with a user's own body part. For example, images of a user's body part may be captured, or may have previously been captured (e.g., in prior appointments, etc.), and converted into virtual, three-dimensional, form. In such a situation, the virtual body part may substantially resemble the visual appearance of the user's own body part (e.g., skin color, size, blemishes, etc.).

At 302, an embodiment may receive manipulation input associated with the virtual object. Responsive to receiving, at 302, the manipulation input, an embodiment may perform, at 304, at least one function associated with the virtual object. In an embodiment, the manipulation input may be associated with a way the user interacts with the virtual object and may be received during the conversational session. In an embodiment, the manipulation input may be provided using at least one of a plurality of interaction methods. For example, the manipulation input may be provided using augmented touch input. The augmented touch input may be provided with or without the presence of an additional wearable device (e.g., physical gloves operatively coupled to the AR/VR enabled device, etc.). For example, a user utilizing a wearable headset (e.g., Google Glass®, etc.) to visualize a virtual torso may also be wearing a pair of dedicated AR/VR gloves that are configured to track a user's real-world spatial hand movements and identify a corresponding location in the augmented and/or virtual space. Therefore, if the virtual torso appears approximately 3 feet in front of the user, a user may reach out 3 feet in front of them to provide input and/or interact with the virtual torso. Other manipulation input methods may also be utilized such as touch input provided to a display screen (e.g., for a virtual object displayed on the display screen, etc.), mechanical input provided to a mechanical mouse, and the like. The manipulation input may be received in addition to or in lieu of additional types of input (e.g., voice input, text input, etc.).

In an embodiment, the manipulation input may comprise user selection input. The user selection input may be associated with an area of the virtual object. For example, a use-case may involve a medically-based digital assistant that queries the user to identify a location on a virtual torso where they feel pain. A user may then subsequently provide a selection input to the virtual torso by touching (e.g., using augmented touch input, etc.) the area of the virtual torso that corresponds to the location where they feel pain, for example, the location of the appendix (e.g., the lower right abdomen, etc.). In another example, the selection input may be a user-provided outline of the desired area. For example, a user may draw, using a finger, a circle around the area of the virtual torso where they feel pain.

Responsive to receiving the selection input, an embodiment may perform a corresponding function. The corresponding function may be, for example, a highlight function associated with the selected area. The highlight function may visually distinguish the selected area of the virtual torso from the non-selected areas (e.g., by changing the color of the selected area, zoom in on the selected area, darken non-selected areas, etc.). For example, responsive to receiving a selection input associated with an area corresponding to the appendix, an embodiment may highlight a predetermined radius around the selected area (e.g., 2 inches in each direction around the selected area, etc.). In another example, responsive to receiving a user outline of an area associated with the virtual torso, an embodiment may highlight the outlined area.

In an embodiment, the manipulation input may comprise user provided rotational input. The rotational input may be associated with a way the virtual object is moved (e.g., rotated around an axis, rotated horizontally, inverted, etc.). The rotational input may be provided using one of a variety of different methods. In one example, a user may perform a predetermined gesture movement to rotate the virtual torso (e.g., a swipe gesture, a two-handed rotational gesture, etc.). In another example, a user may select one of a plurality of directional buttons (e.g., physical and/or virtual arrows buttons, etc.). Each directional button may correspond to a direction of rotation and the selection of one of the directional buttons may rotate the virtual torso by a predetermined amount in the corresponding direction (e.g., a single selection of a virtual right arrow directional button may rotate the virtual torso by 5 degrees around an axis to the right, etc.). In yet another example, a user may interact with a physical and/or a virtual slide mechanism. A user may drag a button associated with the slide mechanism to the left or right and depending on the direction of the slide the virtual torso rotates accordingly. In an embodiment, the rotational input may be used in conjunction with a user selection input. For example, responsive to receiving the query to identify a location on a virtual torso where the user feel's pain, a user may provide rotational input to the virtual object to rotate the torso until the user identifies the location on the virtual torso where they pain and may then subsequently provide a selection input.

In an embodiment, the virtual object may comprise a plurality of viewable layers. For example, a top layer of the virtual object may be associated with the epidermis whereas secondary ("lower") layers may be associated with particular organs underneath the epidermis. In an embodiment, the manipulation input may comprise a user selection of at least one of the plurality of viewable layers. The selection of at least one of the plurality of layers may be provided using one of a variety of different methods. For example, a user may perform a predetermined gesture (e.g., a swipe gesture, etc.) to cycle between the layers. In another example, a user may select one of a plurality of different available buttons where each button is associated with a different layer (e.g., button A is associated with the epidermis layer, button B is associated with the muscle layer, button C is associated with the bone layer, etc.).

Responsive to receiving a selection input corresponding to a particular layer, an embodiment may adjust the virtual torso to display aspects associated with that layer. For example, if a virtual torso was originally configured to display the epidermis layer of the torso, responsive to receiving user manipulation input to display the muscle layer, an embodiment may adjust the virtual torso to display the muscles aligned underneath the epidermis layer. In an embodiment, the manipulation input may correspond to the entire torso or, alternatively, may only correspond to a particular area. For example, a user may provide selection input to the virtual torso to identify an area where they feel pain and then subsequently provide input to display the muscle layer of the selected area. In this situation, only a viewable layer of the selected area is changed, whereas the non-selected areas remain unadjusted.

In an embodiment, the manipulation input may comprise assigning a vibrational intensity to at least a portion of the displayed virtual object. The vibrational intensity may correspond to a level of pain a user may be experiencing in a particular area. The vibrational intensity may be assigned using one of a variety of different methods. For example, a device may activate one or more actuators (e.g., haptic sensors, etc.) operatively coupled to the device that may provide vibrational feedback to the user. The vibrational feedback may comprise multiple vibrational levels, where each vibrational level corresponds to a different degree of pain (e.g., a softer vibration level may correspond to a mild pain whereas a stronger vibration level may correspond to a greater pain, etc.). In an embodiment, a user may be able to select the area of the virtual torso where they feel pain and then select the vibrational level that most accurately reflects the intensity of that pain. In an embodiment, the vibrational feedback may correspond to how a user perceives their pain. For example, the vibrational feedback may comprise different lengths of vibration, where each length of vibration corresponds to a particular pain perception (e.g., throbbing pain, constant pain, etc.). A user may be able to select one of these vibration lengths and assign that to the virtual object.

In an embodiment, more than one user may visualize and/or interact with the same virtual object simultaneously. For example, two users may each be wearing a wearable device (e.g., Google Glass®, etc.) and may both see the same virtual object. The two users may then each provide their own manipulation inputs to the virtual object. In an embodiment, any manipulation input provided to the virtual object by one user may be readily visible to the other user(s) (e.g., if a user highlights a portion of the virtual object the highlighted portion may be visible to another user simultaneously visualizing the same virtual object, etc.). In an embodiment, some manipulation inputs provided to the virtual object may only be visible by the provider. For example, in a scenario where the two users are a doctor and a patient, a doctor may provide manipulation input to the virtual object that they do not want the patient to see or think is relevant for the patient to see. These types of "private" manipulation inputs may be designated as such before and/or during provision of the input.

In one embodiment, the input provided by a user may be stored and sent to another user at a later time. For example, rather than both the doctor and the patient interacting with the virtual object at the same time, as described above, the patient alone may view and provide input to the virtual object. The virtual object, including the provided input, may then be transmitted to another location, for example, to a doctor, to a data storage location accessible by a doctor or the patient, transmitted from one doctor to another doctor, or the like. In other words, a particular virtual object may be stored in an accessible database. For example, a database may comprise a plurality of user profiles, where each user profile corresponds to a particular user. A virtual object may be stored in one of the user profiles and accessed upon identifying the user associated with the user profile. In an embodiment the stored virtual object may contain some or all of the manipulation inputs previously provided to it by the user. For example, a stored virtual torso may contain all of the previously selected portions, previously provided vibrational inputs, other previously provided information, etc. Upon accessing the stored virtual torso, all of the previously provided manipulation inputs may be readily displayed and/or apparent to the user.

Responsive to not receiving, at 302, manipulation input, an embodiment may, at 303, do nothing or, alternatively, may simply just display the virtual object.

The various embodiments described herein thus represent a technical improvement to conventional virtual object interaction techniques. Using the techniques described herein, an embodiment may receive manipulation inputs provided to a virtual object by a user. The manipulation inputs may be provided in addition to or in lieu of conventional interaction techniques (e.g., voice input, etc.). An embodiment may then perform a function on the virtual object that corresponds with the manipulation input. Such techniques enhance a user's ability to communicate information by providing them with a greater number of input modalities.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, a system, apparatus, or device (e.g., an electronic, magnetic, optical, electromagnetic, infrared, or semiconductor system, apparatus, or device) or any suitable combination of the foregoing. More specific examples of a storage device/medium include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:
   receiving, at an information handling device, an indication to display a virtual object in association with a conversational session;
   receiving, during the conversational session, user manipulation input associated with the displayed virtual object, wherein the user manipulation input comprises a vibrational intensity assignment to a portion of the displayed virtual object, the vibrational intensity assignment being associated with a pain perception type; and
   performing, based upon the received user manipulation input and responsive to detecting a selection input to the portion of the displayed virtual object, at least one function associated with the portion of the displayed virtual object, wherein the at least one function comprises outputting a vibration that corresponds to the pain perception type;
   wherein the virtual object comprises a three-dimensional virtual object and wherein the three-dimensional virtual object is viewable on a device capable of displaying at least one of: augmented reality data and virtual reality data.

2. The method of claim 1, wherein the virtual object is a representation of a body part.

3. The method of claim 2, wherein the body part is associated with a user's own body part.

4. The method of claim 1, wherein the user manipulation input comprises a selection input associated with an area of the virtual object and wherein the performing the at least one function comprises highlighting the area.

5. The method of claim 1, wherein the user manipulation input comprises a rotation input and wherein the performing the at least one function comprises rotating the virtual object responsive to the rotation input.

6. The method of claim 1, wherein the virtual object comprises a plurality of viewable layers, wherein the user manipulation input comprises selecting at least one of the plurality of viewable layers, and wherein the performing the at least one function comprises displaying the selected layer.

7. The method of claim 1, wherein the conversational session comprises an interactive session with an audible virtual assistant.

8. An information handling device, comprising:
a processor;
a memory device that stores instructions executable by the processor to:
receive an indication to display a virtual object in association with a conversational session;
receive, during the conversational session, user manipulation input associated with the displayed virtual object, wherein the user manipulation input comprises a vibrational intensity assignment to a portion of the displayed virtual object, the vibrational intensity assignment being associated with a pain perception type; and
perform, based upon the received user manipulation input and responsive to detecting a selection input to the portion of the displayed virtual object, at least one function associated with the portion of the displayed virtual object, wherein the at least one function comprises outputting a vibration that corresponds to the pain perception type;
wherein the virtual object comprises a three-dimensional virtual object and wherein the three-dimensional virtual object is viewable on a device capable of displaying at least one of: augmented reality data and virtual reality data.

9. The information handling device of claim 8, wherein the virtual object is a representation of a body part.

10. The information handling device of claim 9, wherein the body part is associated with a user's own body part.

11. The information handling device of claim 8, wherein the user manipulation input comprises a selection input associated with an area of the virtual object and wherein the instructions executable by the processor to perform the at least one function comprise instructions executable by the processor to highlight the area.

12. The information handling device of claim 8, wherein the user manipulation input comprises a rotation input and wherein the instructions executable by the processor to perform the at least one function comprise instructions executable by the processor to rotate the virtual object responsive to the rotation input.

13. The information handling device of claim 8, wherein the virtual object comprises a plurality of viewable layers, wherein the user manipulation input comprises selecting at least one of the plurality of viewable layers, and wherein the instructions executable by the processor to perform the at least one function comprises instructions executable by the processor to display the selected layer.

14. A product, comprising:
a storage device that stores code, the code being executable by a processor and comprising:
code that receives an indication to display a virtual object in association with a conversational session;
code that receives, during the conversational session, user manipulation input associated with the display virtual object, wherein the user manipulation input comprises a vibrational intensity assignment to a portion of the displayed virtual object, the vibrational intensity assignment being associated with a pain perception type; and
code that performs, based upon the received user manipulation input and responsive to detecting a selection input to the portion of the display virtual object, at least one function associated with the portion of the displayed virtual object, wherein the at least one function comprises outputting a vibration that corresponds to the pain perception type;
wherein the virtual object comprises a three-dimensional virtual object and wherein the three-dimensional virtual object is viewable on a device capable of displaying at least one of: augmented reality data and virtual reality data.

15. The product of claim 14, wherein the virtual object is a representation of a body part.

16. The product of claim 14, wherein the user manipulation input comprises a selection input associated with an area of the virtual object and wherein the performing the at least one function comprises highlighting the area.

17. The product of claim 14, wherein the conversational session comprises an interactive session with an audible virtual assistant.

* * * * *